United States Patent
Lee et al.

(10) Patent No.: US 8,821,211 B2
(45) Date of Patent: Sep. 2, 2014

(54) DEVICE FOR CUTTING OF GLASS SHEET

(75) Inventors: Ho Kyung Lee, Daejeon (KR); Kyu Hwang Lee, Daejeon (KR); Soon Ki Heo, Daejeon (KR)

(73) Assignee: LG Chem, Ltd., Seoul (KR)

( * ) Notice: Subject to any disclaimer, the term of this patent is extended or adjusted under 35 U.S.C. 154(b) by 36 days.

(21) Appl. No.: 13/634,466

(22) PCT Filed: Apr. 20, 2011

(86) PCT No.: PCT/KR2011/002826
§ 371 (c)(1),
(2), (4) Date: Dec. 3, 2012

(87) PCT Pub. No.: WO2011/132929
PCT Pub. Date: Oct. 27, 2011

(65) Prior Publication Data
US 2013/0078891 A1 Mar. 28, 2013

(30) Foreign Application Priority Data

Apr. 21, 2010 (KR) .......................... 10-2010-0036729

(51) Int. Cl.
| | |
|---|---|
| B24B 49/00 | (2012.01) |
| B24B 51/00 | (2006.01) |
| B24B 13/015 | (2006.01) |
| G05B 15/02 | (2006.01) |
| C03B 33/02 | (2006.01) |
| B24B 27/033 | (2006.01) |
| C03B 33/037 | (2006.01) |
| G01N 21/896 | (2006.01) |

(52) U.S. Cl.
CPC .............. *B24B 13/015* (2013.01); *G05B 15/02* (2013.01); *C03B 33/02* (2013.01); *B24B 27/033* (2013.01); *C03B 33/037* (2013.01); *G01N 21/896* (2013.01)
USPC ....................................... 451/5; 451/8; 451/11

(58) Field of Classification Search
USPC ........ 451/41, 43, 44, 57, 58, 5, 8–11; 83/368; 219/121.67; 700/110; 65/29.11, 158
See application file for complete search history.

(56) References Cited

U.S. PATENT DOCUMENTS

| | | | |
|---|---|---|---|
| 4,044,639 A | * | 8/1977 | Kato ................................ 83/880 |
| 4,492,477 A | | 1/1985 | Leser |
| 6,184,924 B1 | | 2/2001 | Schneider et al. |

(Continued)

FOREIGN PATENT DOCUMENTS

| | | |
|---|---|---|
| JP | 06082735 | 3/1994 |
| JP | 08257890 | 10/1996 |

(Continued)

*Primary Examiner* — Dung Van Nguyen
(74) *Attorney, Agent, or Firm* — McKenna Long & Aldridge, LLP

(57) ABSTRACT

Disclosed herein is a device for cutting a glass sheet, continuously supplied after a melting and solidification process, into quadrangular glass substrates. The glass sheet cutting device includes two or more cutters for cutting a glass sheet into quadrangular glass substrates, a defect inspector for scanning the glass sheet to three-dimensionally check defect positions in a length direction, a width direction and a thickness direction of the glass sheet, a position adjuster for moving at least one of the cutters to a portion of the glass sheet at which few defects are distributed, and a controller for informing the position adjuster of positions of the cutters based on the scanned results received from the defect inspector.

24 Claims, 6 Drawing Sheets

(56) References Cited

U.S. PATENT DOCUMENTS

| | | | |
|---|---|---|---|
| 7,553,390 B2 * | 6/2009 | Yamabuchi et al. | 156/257 |
| 8,051,679 B2 * | 11/2011 | Abramov et al. | 65/112 |
| 2004/0060416 A1 | 4/2004 | Luiz | |
| 2004/0134231 A1 * | 7/2004 | Oya | 65/29.11 |

FOREIGN PATENT DOCUMENTS

| | | |
|---|---|---|
| JP | 08327561 | 12/1996 |
| JP | 11337324 | 12/1999 |
| JP | 2000-311924 | 11/2000 |
| JP | 2003-306338 | 10/2003 |
| JP | 2004122351 | 4/2004 |
| JP | 2005053774 | 3/2005 |
| JP | 2007256106 | 10/2007 |
| JP | 2009008564 | 1/2009 |
| KR | 10-1998-0087315 | 12/1998 |
| KR | 10-2004-0105764 | 12/2004 |
| KR | 10-0742273 | 7/2007 |
| WO | 2005122116 A1 | 12/2005 |

* cited by examiner

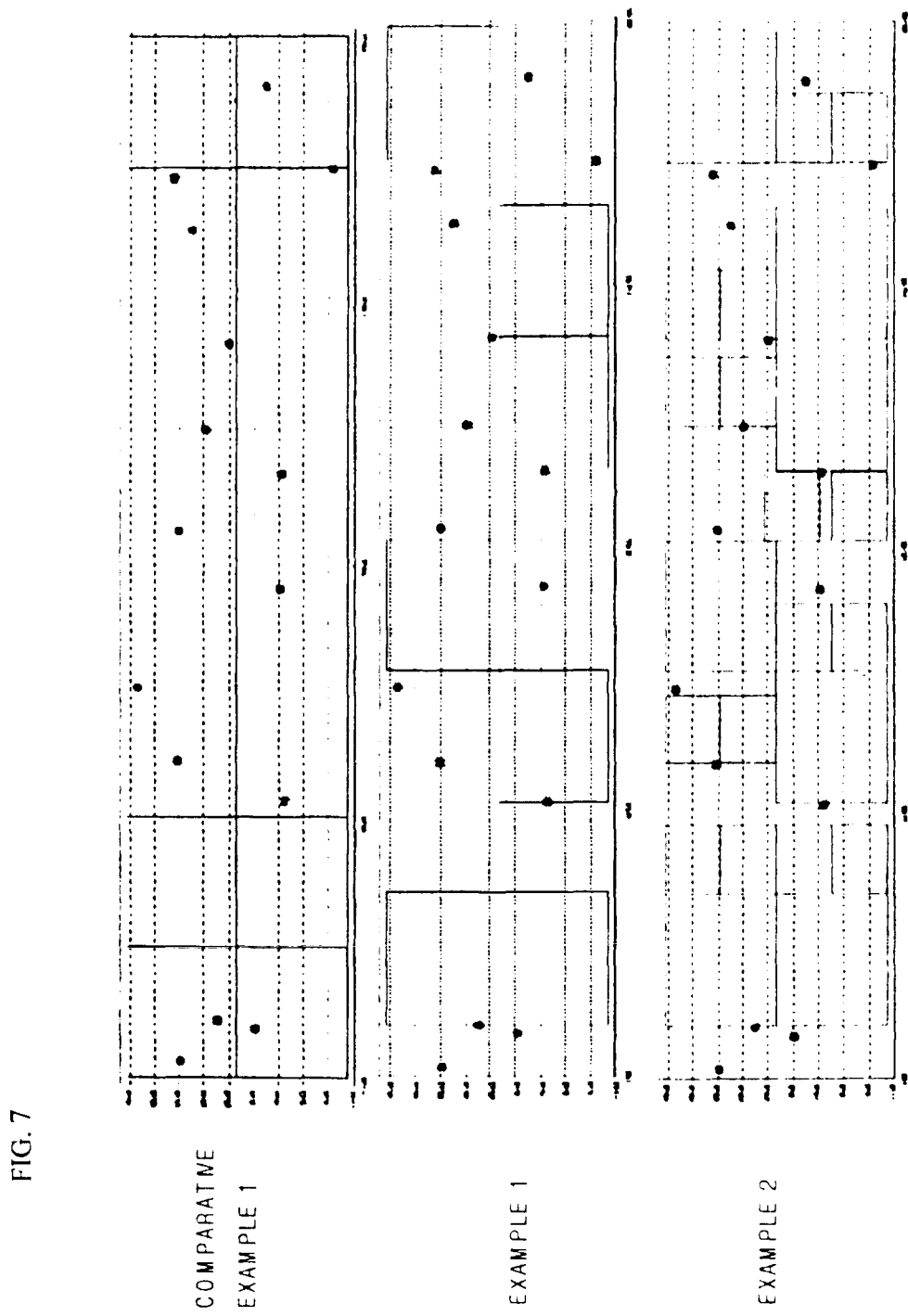

DEVICE FOR CUTTING OF GLASS SHEET

This application is a National Stage Entry of International Application No. PCT/KR2011/002826, filed Apr. 20, 2011, and claims the benefit of Korean Application No. 10-2010-0036729, filed on Apr. 21, 2010, which is hereby incorporated by reference in its entirety for all purposes as if fully set forth herein.

TECHNICAL FIELD

The present invention relates to a glass sheet cutting device, and, more particularly, to a device for cutting a glass sheet, continuously supplied after a melting and solidification process, into quadrangular glass substrates, the glass sheet cutting device including two or more cutters for cutting a glass sheet into quadrangular glass substrates, a defect inspector for scanning the glass sheet to three-dimensionally check defect positions in a length direction, a width direction and a thickness direction of the glass sheet, a position adjuster for moving at least one of the cutters to a portion of the glass sheet at which few defects are distributed, and a controller for informing the position adjuster of positions of the cutters based on the scanned results received from the defect inspector.

BACKGROUND ART

Recently, flat panel displays, such as a liquid crystal display (LCD), a plasma display panel (PDP), and an organic light emitting diode (OLED) have attracted considerable attention.

Glass substrates used to manufacture such flat panel displays are manufactured through a molding process of molding glass molten in a glass smelting furnace in the form of a flat panel and a cutting process of cutting the flat glass panel according to a primary standard. The manufactured glass substrates are transferred to a processing line in which the glass panels are processed. In the processing line, the glass substrates are cut to sizes suitable for the standard of desired flat panel displays, and sharp edges of the glass substrates are ground. Also, quality of the glass substrates manufactured in the processing line is inspected using an inspector to determine whether the glass substrates have defects. If the glass substrates have defects, the glass substrates are destroyed. If the glass substrates have no defects, the glass substrates are shipped as finished products.

Meanwhile, the glass substrates may have defects, such as bubbles, foreign matter, for example stone particles, contamination, scratches, cut chips, and cracks, due to various causes during such a series of molding, cutting and grinding processes of the glass substrates as described above. For this reason, in order to manufacture high-quality flat panel displays, defects of the glass substrates are inspected to sort the glass substrates into good-quality products and defective products, and reasons of defects caused during the manufacturing process are checked and corrected.

Glass substrates are inspected through macrography and optical inspection using a camera and a microscope. Also, the glass substrates are totally inspected, and then some of the inspected glass substrates are sampled so as to secure accuracy and reliability of the inspection.

The macrography to inspect defects of the glass substrates is generally performed at an inspection station installed separately from a transfer line of the glass substrates. An inspector unloads a glass substrate from the transfer line and loads the unloaded glass substrate to the inspection station using a handler, and inspects defects of the glass substrate using a lighting device, such as a fluorescent lamp or a halogen lamp, provided in the inspection station. However, the glass substrate may be scratched or cracked due to physical contact and shock during loading and unloading of the glass substrate using the handler. Also, a lot of time is needed, thereby reducing productivity. In particular, it is increasingly difficult to handle glass substrates due to the increase in size and the decrease in thickness of the glass substrates. For this reason, it takes much time and manpower to inspect the glass substrates.

Consequently, there is a high necessity for a glass sheet cutting device that scans a glass sheet to three-dimensionally check defect positions of the glass sheet in the length direction, the width direction and the thickness direction of the glass sheet during a continuous cutting process and cuts the glass sheet into various kinds of glass substrates, thereby lowering a defect rate, preventing waste, and reducing manufacturing costs.

DISCLOSURE

Technical Problem

Therefore, the present invention has been made to solve the above problems, and other technical problems that have yet to be resolved.

Specifically, it is an object of the present invention to provide a glass sheet cutting device configured so that, when a glass sheet is cut into glass substrates, the glass sheet is scanned using the defect inspector to three-dimensionally check defect positions in the length direction, the width direction and the thickness direction of the glass sheet, and at least one of the cutters is moved to a portion of the glass sheet at which few defects are distributed to manufacture a plurality of glass substrates, thereby maximizing yield of the glass substrates.

Also, it is another object of the present invention to provide a glass sheet cutting device for cutting a glass sheet into at least two kinds of glass substrates, thereby improving yield of the glass substrates and reducing manufacturing costs.

Technical Solution

In accordance with one aspect of the present invention, the above and other objects can be accomplished by the provision of a device for cutting a glass sheet, continuously supplied after a melting and solidification process, into quadrangular glass substrates, the glass sheet cutting device including two or more cutters for cutting a glass sheet into quadrangular glass substrates, a defect inspector for scanning the glass sheet to three-dimensionally check defect positions in a length direction, a width direction and a thickness direction of the glass sheet, a position adjuster for moving at least one of the cutters to a portion of the glass sheet at which few defects are distributed, and a controller for informing the position adjuster of positions of the cutters based on the scanned results received from the defect inspector.

The glass sheet cutting device according to the present invention scans a glass sheet to three-dimensionally check defect positions in the length direction, the width direction and the thickness direction of the glass sheet, moves at least one of the cutters to a portion of the glass sheet at which few defects are distributed, and cuts the glass sheet into quadrangular glass substrates. Consequently, it is possible to efficiently manufacture glass substrates during a continuous mass-production process while minimizing a defect rate of the glass substrates.

Also, the defect inspector three-dimensionally checks defect positions of the glass sheet to decide positions of the cutters. Consequently, it is possible to properly move the cutters based on the defect positions and to perform a continuous cutting process.

The kind of the cutters is not particularly restricted so long as the cutters have a structure or characteristics to cut the glass sheet into quadrangular glass substrates. A representative example of each of the cutters may be a diamond knife or a light source for cutting, such as a laser.

In a preferred example, the cutters may include a first cutter for cutting the glass sheet in the width direction ('Y direction') into first glass substrates, a second cutter for cutting each of the first glass substrates in the length direction ('X direction') into second glass substrates, a third cutter for cutting each of the second glass substrates in the width direction ('X direction') into third glass substrates, and a fourth cutter for cutting the third glass substrates in the length direction ('Y direction').

For example, the first cutter may be moved to a portion of the glass sheet at which few defects are distributed in the length direction ('X direction') to cut the glass sheet into the first glass substrates, thereby improving yield of the first glass substrates.

For example, the second cutter may cut each of the first glass substrates into second glass substrates having no defects when each of the first glass substrates has no defects, thereby easily manufacturing good-quality second glass substrates. The size of each of the second glass substrates may be decided based on, for example, product specifications.

For example, the third cutter may cut each of the second glass substrates into a third glass substrate having defects and a third glass substrate having no defects when each of the second glass substrates has defects.

For example, the fourth cutter may cut the third glass substrate having defects to remove the defects from the third glass substrate, thereby easily manufacturing good-quality fourth glass substrates. The size of each of the fourth glass substrates may be decided based on, for example, product specifications.

In a preferred example, the fourth cutter may cut the third glass substrate having defects from one end or opposite ends of the third glass substrate within a range of less than 30% of the length of the third glass substrate to remove the defects from the third glass substrate. More preferably, the portion of the third glass substrate having defects extends from one end or opposite ends of the third glass substrate within a range of 0.1 to 30% of the length of the third glass substrate.

Meanwhile, among the third glass substrates, a defective glass substrate having defects located at a portion that cannot be removed by the fourth cutter may be destroyed.

In the above structure, the width of the defective glass substrate may be 20% or less, preferably 0.1% to 20%, of the size of the glass substrate having no defects to minimize the size of the defective glass substrate.

Meanwhile, the defect inspector may be disposed ahead of the cutters, preferably, in the length direction of the glass sheet. Consequently, an inspection process is performed before the cutters cut the glass sheet, thereby greatly improving yield as compared with a conventional glass sheet cutting device that performs an inspection process after cutting the glass sheet.

In particular, the characteristic of the defect inspector for three-dimensionally checking defects of the glass sheet in consideration of the thickness direction (Z direction as well as the length direction (X direction) and the width direction (Y direction) of the glass sheet during the inspection process of inspecting the defects of the glass sheet is a novel concept that can be seen from the conventional glass sheet cutting device.

In a preferred example, the defect inspector may include two or more cameras for checking the defect positions of the glass sheet in the length direction, the width direction and the thickness direction of the glass sheet. The number of the cameras may be varied depending upon the width of the glass sheet. Preferably, the defect inspector includes 2 to 30 cameras.

The cameras may measure distances and angles between the cameras and the defects to check the defect positions. Specifically, the defect inspector includes two or more cameras to three-dimensionally measure angles and straight distances between the cameras and each defect. Consequently, it is possible to accurately check position coordinates (X, Y, Z) of each defect using the measured angles and straight distances.

The defects may occur in various forms. For example, the defects may include fish eyes, bubbles, black dots, white dots, or protrusions or grooves formed at the outer surface of the glass sheet.

Meanwhile, the defects located at the outer surface, i.e. the top or bottom, of the glass sheet are excluded from objects to be cut. For example, defects located at the top or bottom of the glass sheet may be removed by grinding during a post processing process. Consequently, the defects are excluded from objects to be cut, thereby improving productivity. According to circumstances, only defects located at the bottom of the glass sheet may be removed by grinding during the post processing process, and defects located at the top of the glass sheet may be sorted as objects to be cut.

In a preferred example, the controller may include an arrangement server for performing mixed integer linear programming based on positional information of the defects input by the defect inspector to imaginarily arrange glass substrates on the glass sheet. Consequently, it is possible to set a plan for optimally arranging glass substrates with the respect to a glass sheet.

For example, in the mixed integer linear programming, restrictive conditions may include X, Y, Z coordinates of defects, the kind and size of a glass substrate, and the size of a glass sheet, and an objective function may be set to maximize space utilization of the glass substrate.

In a concrete example, a mixed integer linear programming model may be defined as follows.

$$\text{Objective function: Maximize} \sum_k L_k \times H_k \times Z_k \quad \text{Expression (1)}$$

Restrictive Conditions:

$$X_{k2} = X_{k1} + L_k \quad \text{Expression (2)}$$

$$Y_{k2} = Y_{k1} \quad \text{Expression (3)}$$

$$X_{k3} = X_{k1} \quad \text{Expression (4)}$$

$$X_{k3} = Y_{k1} - H_k \quad \text{Expression (5)}$$

$$X_{k4} = X_{k2} \quad \text{Expression (6)}$$

$$Y_{k4} = Y_{k3} \quad \text{Expression (7)}$$

$$-M \times (2 - Z_k Z_{k'}) + X_{k2} \leq X_{k'1} + M \times (1 - ZZ_{kk'1}) \quad \text{Expression (8)}$$

$$-M \times (2-Z_k-Z_{k'}) + X_{k'2} \leq X_{k1} + M \times (1-ZZ_{kk'2}) \qquad \text{Expression (9)}$$

$$M \times (2-Z_k-Z_{k'}) + Y_{k1} \geq Y_{k'3} - M \times (1-ZZ_{kk'3}) \qquad \text{Expression (10)}$$

$$M \times (2-Z_k-Z_{k'}) + Y_{k'1} \geq Y_{k3} - M \times (1-ZZ_{kk'4}) \qquad \text{Expression (11)}$$

Definition of Variables $Z_k$: 1 or 0 if a quadrangle k is valid
$ZZ_{kk'm}$: Positional relationship between two quadrangles k and k' (m=1, 2, 3, 4)
$X_{kn}$: X coordinate of a defect n of a quadrangle k (n=1, 2, 3, 4)
$Y_{kn}$: Y coordinate of a defect n of a quadrangle k (n=1, 2, 3, 4)
k: A set of all quadrangles having defects
$L_k$: Length of a quadrangle k
$H_k$: Height of a quadrangle k
M: Very large number to express validity of 0-1 variables In the above model, Expression (2) to Expression (7) are restrictive conditions to show positional relationships between for corner points in a quadrangle k, and Expression (8) to Expression (11) are restrictive conditions to show positional relationships between two quadrangles k and k'.

Here, m=1 means that the quadrangle k is located at the left side of the quadrangle k' and m=2 means that the quadrangle k is located at the right side of the quadrangle k'. Also, m=3 means that the quadrangle k is located at the upper side of the quadrangle k' and m=4 means that the quadrangle k is located at the lower side of the quadrangle k'. M is a variable to exclude an infeasible solution from the mixed integer linear programming However, the above-mentioned mixed integer linear programming model is an illustrative example. Those skilled in the art to which the present invention pertains can set various mixed integer linear programming models based on the disclosure of the present invention, and therefore, the scope of the present invention is not limited to the illustrative example.

According to circumstances, the glass sheet cutting device may further include a thickness inspector for checking unevenness of the outer surface of the glass sheet. In a concrete example, the thickness inspector may include a sensor. Consequently, it is possible to measure an index of refraction of the glass sheet when light is transmitted through the glass sheet and to check unevenness of the outer surface of the glass sheet based on the measured index of refraction.

In a preferred example, if the unevenness of the outer surface of the glass sheet is 1% or more of the thickness of the glass sheet, the unevenness may be regarded as defects to be removed.

That is, if the unevenness of the outer surface of the glass sheet is 1% or more of the thickness of the glass sheet, it is not possible to obtain a good-quality glass sheet by grinding. For this reason, the unevenness is regarded as defects to be removed, thereby improving a quality rate of glass substrates.

In another preferred example, the thickness inspector may be positioned between the defect inspector and the cutters. Consequently, it is possible to measure the coordinates of defects using the defect inspector and, in addition, to check defects due to the unevenness of the glass sheet using the thickness inspector, thereby improving a quality rate of glass substrates.

The glass substrates are not particularly restricted so long as the glass substrates can be used to manufacture flat panel displays. Preferably, each of the glass substrate is a glass panel for liquid crystal displays (LCDs), a glass panel for organic light emitting diodes (OLEDs) or a glass panel for plasma display panels (PDPs).

On the other hand, the glass sheet cutting device may include a first production line to produce relatively large glass substrates, from which defects have been removed and a second production line to produce relatively small glass substrates, from which defects have been removed.

The second production line may diverge from the first production line so that good-quality products and defective products can be easily divided.

In accordance with another aspect of the present invention, there is provided a glass substrate manufacturing method. In a concrete example, there is provided a method of manufacturing quadrangular glass substrates from a glass sheet, which is continuously supplied after a melting and solidification process, the glass sheet manufacturing method including an inspection process of scanning the glass sheet using a defect inspector to three-dimensionally check the positions of defects in a length direction, a width direction and a thickness direction of the glass sheet, a first division process of cutting the glass sheet in the width direction ('X direction') using a first cutter to divide the glass sheet into first glass substrates, a second division process of cutting each of the first glass substrates in the length direction ('Y direction') using a second cutter to divide each of the first glass substrates into second glass substrates, a third division process of cutting each of the second glass substrates in the width direction ('X direction') using a third cutter to divide each of the second glass substrates into third glass substrates, a fourth cutting process of cutting each of the third glass substrates in the length direction ('Y direction') using a fourth cutter, and a post processing process of grinding surfaces of glass substrates obtained in the fourth cutting process to remove defects that have been sorted as ones that can be removed in the inspection process.

For example, the good-quality second glass substrates obtained through the second division process may be glass substrates for large-sized LCDs, the good-quality third glass substrates obtained through the third division process may be glass substrates for middle-sized LCDs, and the good-quality fourth glass substrates obtained through the fourth cutting process may be glass substrates for small-sized LCDs. According to circumstances, the third glass substrates may be half-finished products used to manufacture the fourth glass substrates as the finished products. Similarly, the second glass substrates may be half-finished products used to manufacture the third glass substrates and/or the fourth glass substrates as the finished products.

For example, the first cutter may be moved to a portion of the glass sheet at which few defects are distributed in the length direction ('X direction') to cut the glass sheet into the first glass substrates.

For example, the second cutter may cut each of the first glass substrates into second glass substrates having no defects when each of the first glass substrates has no defects.

For example, the third cutter may cut each of the second glass substrates into a third glass substrate having defects and a third glass substrate having no defects when each of the second glass substrates has defects.

For example, the fourth cutter may cut the third glass substrate having defects to remove the defects from the third glass substrate.

The glass sheet manufacturing method may further include an arrangement process of performing mixed integer linear programming after performing the inspection process to imaginarily arrange glass substrates on the glass sheet.

In this case, the restrictive expression of the mixed integer linear programming may include X, Y, Z coordinates of defects, the kind and size of the glass substrate, and the size of the glass sheet, and the objective expression of the mixed integer linear programming may be configured to maximize space utilization of the glass substrate.

DESCRIPTION OF DRAWINGS

The above and other objects, features and other advantages of the present invention will be more clearly understood from the following detailed description taken in conjunction with the accompanying drawings, in which:

FIGS. 6 and 7 are a graph and a typical plan view showing comparison between illustrative examples of the present invention and a comparative example.

BEST MODE

Now, preferred embodiments of the present invention will be described in detail with reference to the accompanying drawings. It should be noted, however, that the scope of the present invention is not limited by the illustrated embodiments.

Figure 1:
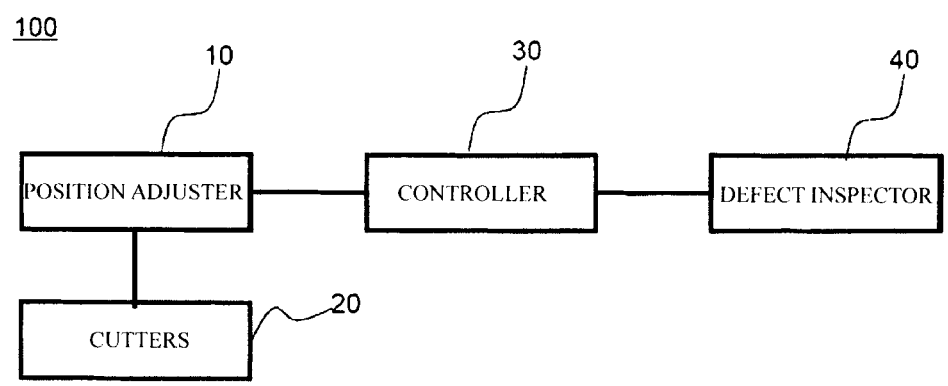
FIG. 1 is a view showing the construction of a glass sheet cutting device according to an embodiment of the present invention.

FIG. 1 is a view typically showing the construction of a glass sheet cutting device according to an embodiment of the present invention.

Referring to FIG. 1, a glass sheet cutting device 100 includes cutters 20, a defect inspector 40, a position adjuster 10 and a controller 30.

The cutters 20 cut a glass sheet into quadrangular glass substrates, and the position adjuster 10 moves at least one of the cutters to a portion of the glass sheet at which few defects are distributed.

The defect inspector 40 scans the glass sheet to three-dimensionally check defect positions of the glass sheet in the length direction, the width direction and the thickness direction of the glass sheet.

Also, the defect inspector 40 transmits scanned results, i.e. information on the defect positions indicated by an X coordinate, Y coordinate and X coordinate, to the controller 30.

The defect inspector 40 captures the shapes of defects using cameras to determine whether the defects are located inside or outside the glass sheet.

The controller 30 informs the position adjuster 10 of positions of the cutters 20 based on the scanned results received from the defect inspector 40 and divides the defects received from the defect inspector 40 into a defect necessary to be repaired, a defect having good conditions, a defect having poor conditions and a defect having conditions that are difficult to determine.

Also, the controller 30 includes an arrangement server (not shown) for performing mixed integer linear programming based on positional information of the defects input by the defect inspector 40 to imaginarily arrange glass substrates on the glass sheet.

Figure 2:
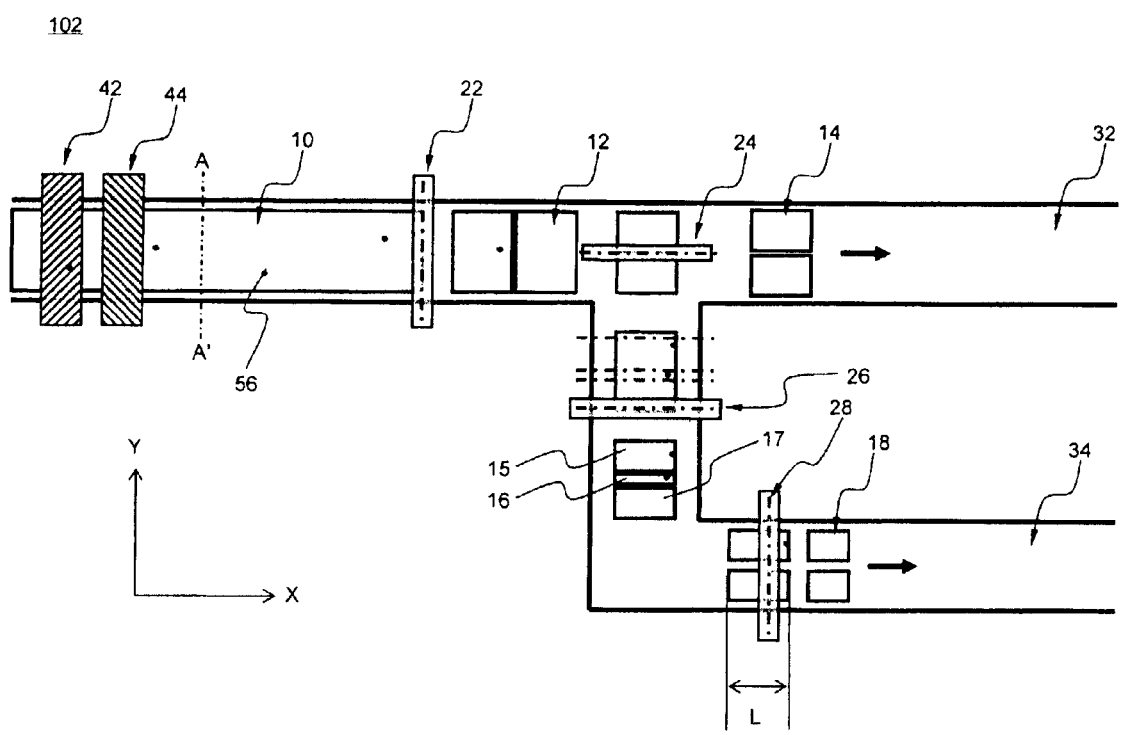
FIG. 2 is a view showing the arrangement of a glass sheet cutting device according to an embodiment of the present invention.
Figure 3:
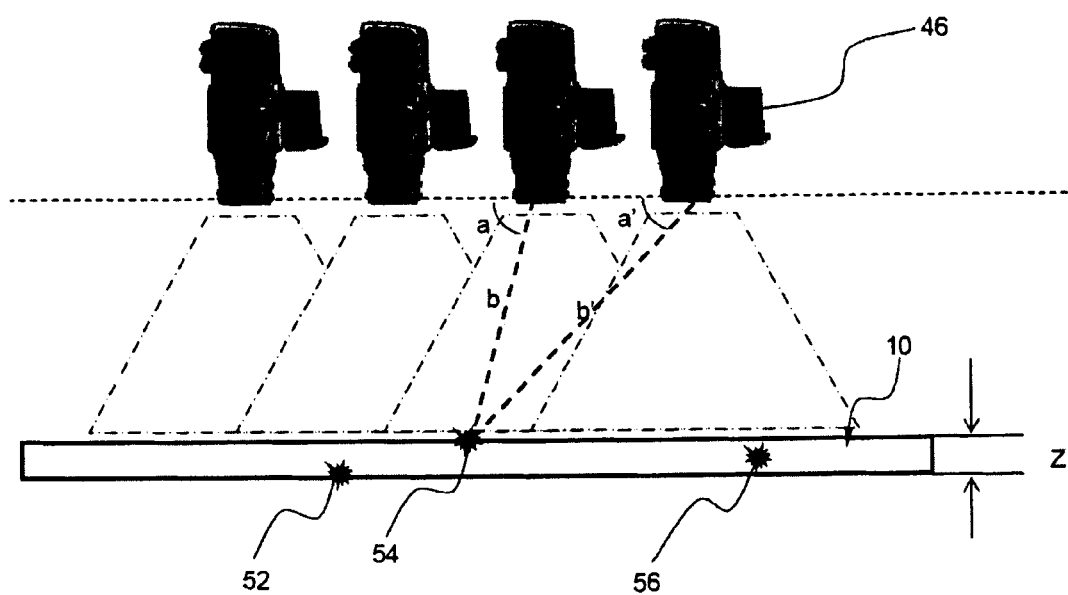
FIG. 3 is a vertical sectional view typically showing a defect inspector of FIG. 2.
Figure 4:
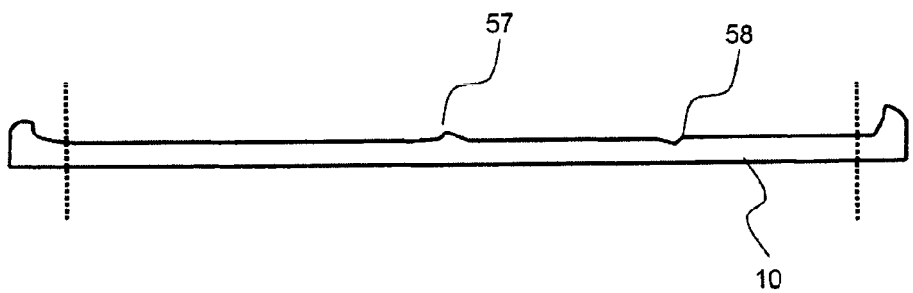
FIG. 4 is a vertical sectional view taken along line A-A' of FIG. 2.

FIG. 2 is a view typically showing the arrangement of a glass sheet cutting device according to an embodiment of the present invention. FIG. 3 is a vertical sectional view typically showing a defect inspector of FIG. 2. Also, FIG. 4 is a vertical sectional view taken along line A-A' of FIG. 2.

Referring to these drawings, a glass sheet cutting device 102, which is a device for cutting a glass sheet 10, continuously supplied after a melting and solidification process, into quadrangular glass substrates 14 and 18, includes four cutters 22, 24, 26 and 28 including position adjusters, a defect inspector 42, a thickness inspector 44 and a controller (not shown).

The cutters 22, 24, 26 and 28 include a first cutter 22 to cut the glass sheet 10 in the width direction ('Y direction') into first glass substrates 12, a second cutter 24 to cut each of the first glass substrates 12 in the length direction ('X direction') into second glass substrates 14, a third cutter 26 to cut each of the second glass substrates 14 in the width direction ('X direction') into third glass substrates 15 and 16, and a fourth cutter 28 to cut the third glass substrates 15 and 16 in the length direction ('Y direction').

Also, the first cutter 22 cuts the glass sheet 10 into first glass substrates 12 at the same intervals irrespective of defect positions, and the second cutter 24 cuts each of the first glass substrates 12 into second glass substrates 14 having no defects when each of the first glass substrates 12 has no defects.

The third cutter 26 cuts each of the second glass substrates 14 into a third glass substrate 15 having defects and a third glass substrate 17 having no defects when each of the second glass substrates 14 has defects. The fourth cutter 28 cuts the third glass substrate 15 to remove defects from the third glass substrate 15.

Also, the fourth cutter 28 cuts the third glass substrate 15 from one end of the third glass substrate 15 within a range of less than 20% of the length L of the third glass substrate 15 to remove defects from the third glass substrate 15.

Among the third glass substrates 15, 16 and 17, the defective glass substrate 16 having defects located at a portion that cannot be removed by the fourth cutter 28 is destroyed. The width of the defective glass substrate 16 is 10% or less of the size of the third glass substrate 17 having no defects to minimize the size of the defective glass substrate 16, which will be destroyed.

The defect inspector 42 is disposed ahead of the first cutter 22 in the length direction X of the glass sheet 10. The defect inspector 42 includes four or more cameras 46 to check defect positions of the glass sheet 10 in the length direction, the width direction and the thickness direction of the glass sheet 10.

The respective cameras 46 measure distances b and b' and angles a and a' between the respective cameras and defects 52, 54 and 56 to check the defect positions.

The defects 52, 54 and 56 include defects 52 and 54 located at the top and bottom of the glass sheet 10 and a defect 56 located in the glass sheet 10. The defects 52 and 54 located at the top and bottom of the glass sheet 10 are removed in a grinding process, as a post processing process. Consequently, the defects 52 and 54 are excluded from objects to be cut.

The thickness inspector 44 is positioned between the defect inspector 44 and the first cutter 22 to check unevenness of the outer surface of the glass sheet 10. If uneven portions 57 and 58 formed at the outer surface of the glass sheet 10 occupies, for example, 1% or more of the thickness of the glass sheet 10, i.e. the uneven portions are defects that can be removed in the grinding process, which is the post processing process, the defects are removed from the glass sheet 10.

Meanwhile, the glass sheet cutting device 102 includes a first production line 32 to produce relatively large second glass substrates 14, from which defects have been removed, and a second production line 34 to produce relatively small fourth glass substrates 18, from which defects have been removed.

Also, the second production line 34 diverges from the first production line 32.

Figure 5:
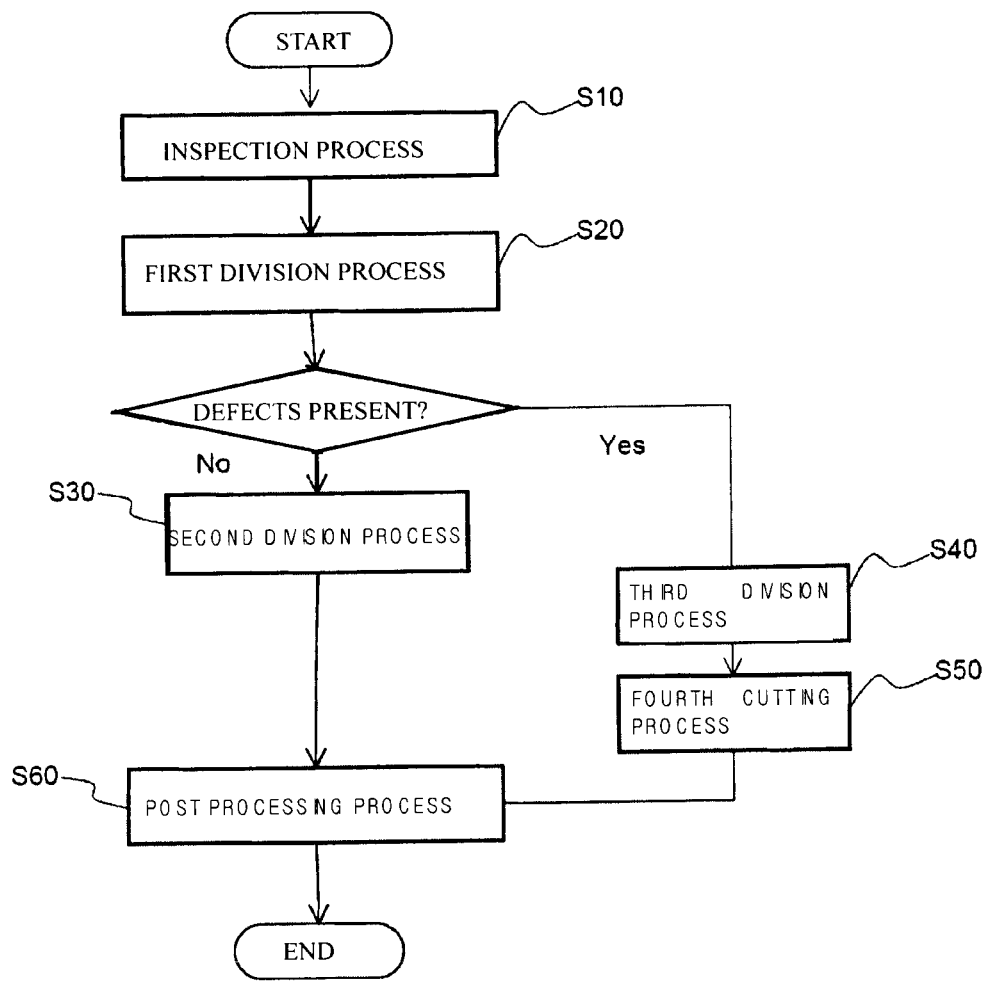
FIG. 5 is a flow chart showing a glass sheet manufacturing method according to an embodiment of the present invention.

FIG. 5 is a flow chart typically showing a glass sheet manufacturing method according to an embodiment of the present invention.

Referring to FIG. 5 together with FIGS. 2 and 3, the glass sheet manufacturing method, which is a method of manufacturing quadrangular glass substrates 14 and 18 from a glass sheet 10, which is continuously supplied after a melting and solidification process, includes an inspection process (S10) of scanning the glass sheet 10 using the defect inspector 42 to three-dimensionally check the positions of defects 52, 54 and 56 in the length direction, the width direction and the thickness direction of the glass sheet 10, a first division process (S20) of cutting the glass sheet 10 in the width direction ('X direction') using the first cutter 22 to divide the glass sheet 10 into first glass substrates 12, a second division process (S30) of cutting each of the first glass substrates 12 in the length direction ('Y direction') using the second cutter 24 to divide each of the first glass substrates 12 into second glass substrates 14, a third division process (S40) of cutting each of the second glass substrates 14 in the width direction ('X direction') using the third cutter 26 to divide each of the second glass substrates 14 into third glass substrates 15, a fourth cutting process (S50) of cutting each of the third glass substrates 15 in the length direction ('Y direction') using the fourth cutter 28, and a post processing process (S60) of grinding the surfaces of glass substrates obtained in the fourth cutting process (S50) to remove defects that have been sorted as ones that can be removed in the inspection process (S10).

Also, the first cutter 22 cuts the glass sheet 10 into first glass substrates 12 at the same intervals irrespective of defect positions, and the second cutter 24 cuts each of the first glass substrates 12 into second glass substrates 14 having no defects when each of the first glass substrates 12 has no defects.

The third cutter 26 cuts each of the second glass substrates 14 into a third glass substrate 15 having defects and a third glass substrate 17 having no defects when each of the second glass substrates 14 has defects. The fourth cutter 28 cuts the third glass substrate 15 to remove defects from the third glass substrate 15.

Hereinafter, the present invention will be described in more detail based on experiments; however, the following experiments are given only to illustrate the present invention, and therefore, the scope of the present invention is not limited to the experiments.

Example 1

Mixed integer linear programming was performed in consideration of the size of glass substrates for A type liquid crystal displays (LCDs) to arrange glass substrates for A type LCDs at positions having no defects on a glass sheet. In an objective expression of the mixed integer linear programming, the area efficiency of the glass substrates for A type LCDs was maximized. In a restrictive expression of the mixed integer linear programming, computer simulation was carried out using the size and defect coordinates (X, Y, Z) of the glass substrates for A type LCDs.

Example 2

The same method as in Example 1 was used except that the size of the glass substrates for B type LCDs, the size of which is half that of the glass substrates for A type LCDs was considered in an objective expression of the mixed integer linear programming, and the area efficiency of the glass substrates for B type LCDs was maximized in a restrictive expression of the mixed integer linear programming, in a state in which the glass substrates for A type LCDs were arranged on the glass sheet based on the results obtained in Example 1.

COMPARATIVE EXAMPLE 1

Glass substrates for A type LCDs were sequentially arranged on a glass sheet from the left end to the right end of the glass sheet in the length direction of the glass sheet based on the size of the glass substrates for A type LCDs without using mixed integer linear programming

EXPERIMENTAL EXAMPLE 1

Figure 6:
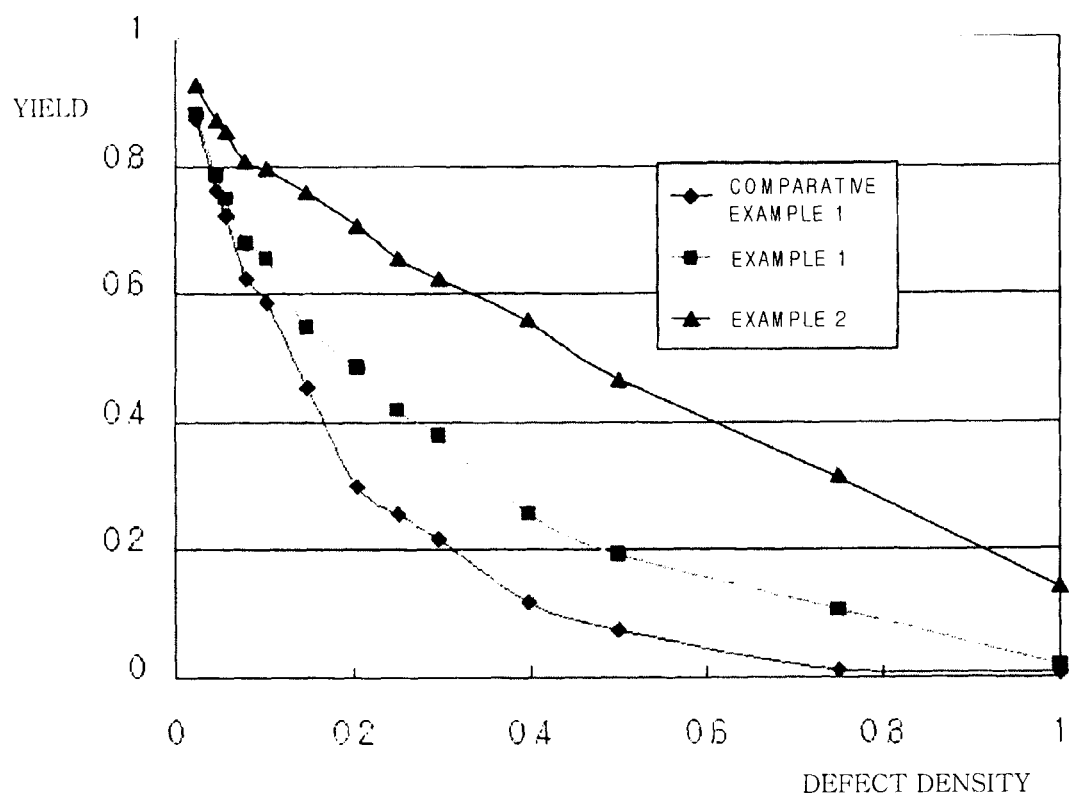

The cutting results based on the arrangement of the glass substrates performed in the above examples and comparative example are shown in FIGS. 6 and 7.

First, referring to FIG. 6, it can be seen that yield of the glass substrates was decreased as the defect density of the glass substrates according to the examples and Comparative example 1 was increased, but the yield of the glass substrates according to Examples 1 and 2 was more slowly decreased than that of the glass substrates according to Comparative example 1.

Subsequently, referring to FIG. 7 together with FIG. 6, it can be seen that, when the defect density was 0.17, the yield of Comparative example 1 was approximately 25%, the yield of Example 1 was approximately 43%, and the yield of Example 2 was approximately 69%. Consequently, it can be seen that, when the glass sheet cutting device according to the present invention is used, yield is sharply increased with the result that it is possible to greatly reduce manufacturing costs.

Specifically, it can be seen that six good-quality glass substrates for A type LCDs were produced according to Comparative example 1, and seven good-quality glass substrates for A type LCDs were produced according to Example 1. Also, it can be seen that seven good-quality glass substrates for A type LCDs were produced and, at the same time, sixteen good-quality glass substrates for B type LCDs were produced according to Example 2.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

As is apparent from the above description, the glass sheet cutting device according to the present invention is configured so that, when a glass sheet is cut into quadrangular glass substrates, the glass sheet is scanned using the defect inspector to three-dimensionally check defect positions in the length direction, the width direction and the thickness direction of the glass sheet, and at least one of the cutters is moved to a portion of the glass sheet at which few defects are distributed to manufacture a plurality of glass substrates. Consequently, it is possible to maximize yield of the glass substrates.

Also, the glass sheet is cut into at least two kinds of glass substrates. Consequently, it is possible to improve yield of the glass substrates, thereby greatly reducing manufacturing costs.

The invention claimed is:

1. A device for cutting a glass sheet, continuously supplied after a melting and solidification process, into quadrangular glass substrates, the glass sheet cutting device comprising:
    two or more cutters for cutting a glass sheet into quadrangular glass substrates;
    a defect inspector for scanning the glass sheet to three-dimensionally check defect positions in a length direction, a width direction and a thickness direction of the glass sheet;
        a position adjuster for moving at least one of the cutters to a portion of the glass sheet at which few defects are distributed; and
        a controller for informing the position adjuster of positions of the cutters based on the scanned results received from the defect inspector,
    wherein the cutters comprise:
    a first cutter for cutting the glass sheet in the width direction ('Y direction') into first glass substrates;
    a second cutter for cutting each of the first glass substrates in the length direction ('X direction') into second glass substrates;
    a third cutter for cutting each of the second glass substrates in the width direction ('X direction') into third glass substrates; and
    a fourth cutter for cutting the third glass substrates in the length direction ('Y direction').

2. The glass sheet cutting device according to claim 1, wherein each of the cutters is a diamond knife or a light source for cutting.

3. The glass sheet cutting device according to claim 2, wherein the light source for cutting is a laser.

4. The glass sheet cutting device according to claim 1, wherein the first cutter is moved to a portion of the glass sheet at which at which few defects are distributed in the length direction ('X direction') to cut the glass sheet into the first glass substrates.

5. The glass sheet cutting device according to claim 1, wherein the second cutter cuts each of the first glass substrates into second glass substrates having no defects when each of the first glass substrates has no defects.

6. The glass sheet cutting device according to claim 1, wherein the third cutter cuts each of the second glass substrates into a third glass substrate having defects and a third glass substrate having no defects when each of the second glass substrates has defects.

7. The glass sheet cutting device according to claim 6, wherein, among the third glass substrates, a defective glass substrate having defects located at a portion that cannot be removed by the fourth cutter is destroyed.

8. The glass sheet cutting device according to claim 7, wherein the width of the defective glass substrate is 20% or less of the size of the glass substrate having no defects to minimize the size of the defective glass substrate.

9. The glass sheet cutting device according to claim 1, wherein the fourth cutter cuts the third glass substrate having defects to remove the defects from the third glass substrate.

10. The glass sheet cutting device according to claim 9, wherein the fourth cutter cuts the third glass substrate having defects from one end or opposite ends of the third glass substrate within a range of less than 30% of a length of the third glass substrate to remove the defects from the third glass substrate.

11. The glass sheet cutting device according to claim 1, wherein the defect inspector is disposed ahead of the cutters in the length direction of the glass sheet.

12. The glass sheet cutting device according to claim 1, wherein the defect inspector comprises two or more cameras for checking the defect positions of the glass sheet in the length direction, the width direction and the thickness direction of the glass sheet.

13. The glass sheet cutting device according to claim 12, wherein the cameras measure distances and angles between the cameras and the defects to check the defect positions.

14. The glass sheet cutting device according to claim 1, wherein the defects comprise fish eyes, bubbles, black dots, white dots, or protrusions or grooves formed at the outer surface of the glass sheet.

15. The glass sheet cutting device according to claim 1, wherein the defects located at the outer surface, i.e. the top or bottom, of the glass sheet are excluded from objects to be cut.

16. The glass sheet cutting device according to claim 1, wherein the controller comprises an arrangement server for performing mixed integer linear programming based on positional information of the defects input by the defect inspector to imaginarily arrange glass substrates on the glass sheet.

17. The glass sheet cutting device according to claim 1, further comprising a thickness inspector for checking unevenness of the outer surface of the glass sheet.

18. The glass sheet cutting device according to claim 17, wherein, if the unevenness of the outer surface of the glass sheet is 1% or more of the thickness of the glass sheet, the unevenness is regarded as defects to be removed.

19. The glass sheet cutting device according to claim 17, wherein the thickness inspector is positioned between the defect inspector and the cutters.

20. The glass sheet cutting device according to claim 1, wherein each of the glass substrate is a glass panel for liquid crystal displays (LCDs), a glass panel for organic light emitting diodes (OLEDs) or a glass panel for plasma display panels (PDPs).

21. The glass sheet cutting device according to claim 1, wherein the glass sheet cutting device comprises a first production line to produce relatively large glass substrates, from which defects have been removed and a second production line to produce relatively small glass substrates, from which defects have been removed.

22. The glass sheet cutting device according to claim 21, wherein the second production line diverges from the first production line.

23. A method of manufacturing quadrangular glass substrates from a glass sheet, which is continuously supplied after a melting and solidification process, the glass sheet manufacturing method comprising:
    an inspection process of scanning the glass sheet using a defect inspector to three-dimensionally check the positions of defects in a length direction, a width direction and a thickness direction of the glass sheet;
    a first division process of cutting the glass sheet in the width direction ('X direction') using a first cutter to divide the glass sheet into first glass substrates;
    a second division process of cutting each of the first glass substrates in the length direction ('Y direction') using a second cutter to divide each of the first glass substrates into second glass substrates;

a third division process of cutting each of the second glass substrates in the width direction ('X direction') using a third cutter to divide each of the second glass substrates into third glass substrates;

a fourth cutting process of cutting each of the third glass substrates in the length direction ('Y direction') using a fourth cutter; and a post processing process of grinding surfaces of glass substrates obtained in the fourth cutting process to remove defects that have been sorted as ones that can be removed in the inspection process.

24. The glass sheet manufacturing method according to claim 23, further comprising an arrangement process of performing mixed integer linear programming after performing the inspection process to imaginarily arrange glass substrates on the glass sheet.

* * * * *